(12) United States Patent
Moscoso et al.

(10) Patent No.: US 7,687,423 B2
(45) Date of Patent: Mar. 30, 2010

(54) SELECTIVE CATALYST FOR AROMATICS CONVERSION

(75) Inventors: Jaime G. Moscoso, Des Plaines, IL (US); Edwin P. Boldingh, Des Plaines, IL (US); Michael G. Gatter, Des Plaines, IL (US); Susan C. Koster, Des Plaines, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 12/146,847

(22) Filed: Jun. 26, 2008

(65) Prior Publication Data

US 2009/0325785 A1    Dec. 31, 2009

(51) Int. Cl.
*B01J 29/06* (2006.01)

(52) U.S. Cl. .............. 502/60; 502/63; 502/64; 502/66; 502/67; 502/74; 502/77; 502/78; 502/79; 423/700; 423/701; 423/702; 423/704; 423/705; 423/709

(58) Field of Classification Search .......... 502/60, 502/63, 64, 66, 67, 74, 77, 78, 79; 423/700, 423/701, 702, 704, 705, 709
See application file for complete search history.

(56) References Cited

U.S. PATENT DOCUMENTS

| | | | |
|---|---|---|---|
| 3,912,659 A | 10/1975 | Brandenburg et al. | 252/455 Z |
| 6,060,417 A | 5/2000 | Kato et al. | 502/66 |
| 6,137,020 A | 10/2000 | Butler et al. | 585/446 |
| 6,793,911 B2 | 9/2004 | Koegler et al. | 423/716 |
| 6,984,764 B1 * | 1/2006 | Roth et al. | 585/323 |
| 2004/0047803 A1 | 3/2004 | Valtchev et al. | 423/716 |
| 2005/0256355 A1 * | 11/2005 | Merlen et al. | 585/475 |
| 2006/0030477 A1 | 2/2006 | Chaumonnot et al. | 502/64 |
| 2006/0247480 A1 * | 11/2006 | Jan et al. | 585/467 |

FOREIGN PATENT DOCUMENTS

WO    WO 93/08125    4/1993

OTHER PUBLICATIONS

Selvam, T. et al., "Selective isopropylation of biphenyl to 4,4'-DIPB over mordenite (MOR) type zeolite obtained from a layered sodium silicate magadiite" *Catalysis Letters* vol. 94, Nos. 1-2, Apr. 2004, 2004 Plenum Publishing Corporation, pp. 17-24.

Selvam, T., et al., "Synthesis and characterization of mordenite (MOR) zeolite derived from a layered silicate, Na-magadiite" *Impact of Zeolites and Other Porous Materials on the New Technologies at the Beginning of the New Millennium, Part A*, Proceedings of the 2nd International FEZA (Federation of the European Zeolite Associations) Conference (Taormina, Italy, Sep. 1-5, 2002), *Studies in Surface Science and Catalysis*, vol. 142, Elsevier Science B.V., pp. 407-414.

Hincapie, B.O., et al., "Synthesis of mordenite nanocrystals" *Microporous and Mesoporous Materials* 67 (2004), pp. 1-26.

Mohamed, M.M., et al., "Development of catalytic properties of mordenite zeolite via chemical modification" *Current Topics in Catalysis* vol. 4, 2005, pp. 80-99.

* cited by examiner

*Primary Examiner*—Elizabeth D Wood
(74) *Attorney, Agent, or Firm*—David J Piasecki

(57) ABSTRACT

The subject invention comprises a novel UZM-14 catalytic material comprising globular aggregates of crystallites having a MOR framework type with a mean crystallite length parallel to the direction of 12-ring channels of about 60 nm or less and a mesopore volume of at least about 0.10 cc/gram. Catalysts formed from the novel material are particularly effective for the transalkylation of aromatics.

18 Claims, 1 Drawing Sheet

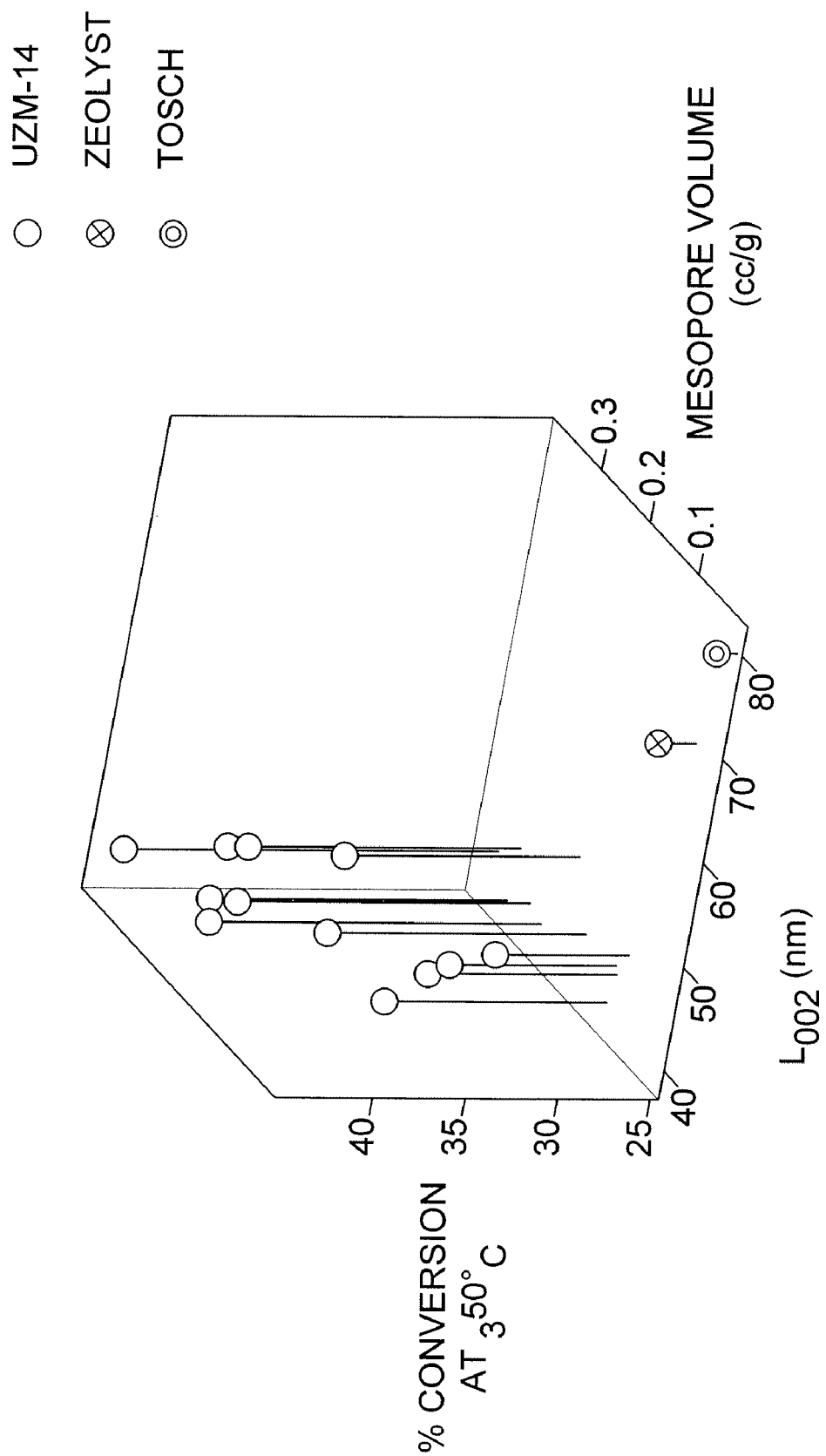

US 7,687,423 B2

SELECTIVE CATALYST FOR AROMATICS CONVERSION

FIELD OF THE INVENTION

This invention relates to a catalyst for the conversion of aromatic hydrocarbons. More specifically, the invention comprises a catalyst with high activity for producing $C_8$ aromatics.

BACKGROUND OF THE INVENTION

Most new aromatics complexes are designed to yield benzene and para-xylene. Benzene is a versatile petrochemical building block used in many different products including ethylbenzene, cumene, and cyclohexane. Para-xylene is also an important building block primarily for the production of polyester fibers, resins, and films formed via terephthalic acid or dimethyl terephthalate intermediates. Since the relative yield of benzene and para-xylene generally does not match the proportions obtained from aromatics-generating processes such as catalytic reforming and cracking, an aromatics complex to obtain these preferred products usually comprises a variety of processes such as one or more of transalkylation, disproportionation, isomerization and dealkylation.

An aromatics complex flow scheme illustrating the use of processes for aromatics conversion is exemplified by Meyers in the Handbook of Petroleum Refining Processes, 3rd. Edition in 2003 by McGraw-Hill.

The known art includes a variety of catalysts effective for converting aromatic feedstocks to desired products. In particular, catalysts have been disclosed for transalkylation to convert lighter aromatics, particularly toluene, and heavier aromatics, especially $C_9$ aromatics, to yield $C_8$ aromatics in order to increase the yield of para-xylene from an aromatics complex. Such transalkylation processes generally are limited in the extent to which they can convert aromatics heavier than $C_9$ to lighter products, and there is a need in the industry for more effective catalysts.

SUMMARY OF THE INVENTION

Broadly, the invention comprises a UZM-14 aggregate material comprising globular aggregates of crystallites having a MOR framework type comprising 12-ring channels, a mesopore volume of at least about 0.10 cc/gram, and a mean crystallite length parallel to the direction of the 12-ring channels of about 60 nm or less.

In a specific embodiment, the invention comprises a catalyst suitable for the conversion of aromatic hydrocarbons which comprises a UZM-14 aggregate material comprising globular aggregates of crystallites having a MOR framework type comprising 12-ring channels, a mesopore volume of at least about 0.10 cc/gram, and a mean crystallite length parallel to the direction of the 12-ring channels of about 60 nm or less; a binder selected from one or more of alumina, silica and silica-alumina; and a metal component comprising one or more elements selected from groups VIB(6), VIIB(7), VIII (8-10) and IVA(14) of the Periodic Table.

In a more specific embodiment, the invention comprises a catalyst suitable for the conversion of aromatic hydrocarbons which comprises a UZM-14 aggregate material comprising globular aggregates of crystallites having a MOR framework type comprising 12-ring channels, a mesopore volume of at least about 0.10 cc/gram, and a mean crystallite length parallel to the direction of the 12-ring channels of about 60 nm or less; an additional zeolitic component selected from one or more of MFI, MEL, EUO, FER, MFS, MTT, MTW, MWW, MAZ, TON, FAU and UZM-8; a binder selected from one or more of alumina, silica and silica-alumina; and a metal component comprising one or more elements selected from groups VIB(6), VIIB(7), VIII(8-10), 1B(11) and IVA(14) of the Periodic Table.

Preferably the UZM-14 aggregate material in each of the above embodiments comprises one or more of the following characteristics: (1) the globular aggregates have a mesopore volume of at least about 0.13 cc/gram; (2) the UZM-14 crystallites have at least about $1 \times 10^{19}$ 12-ring-channel openings/gram of UZM-14 material; (3) the mean crystallite length parallel to the direction of the 12-ring channels is about 50 nm or less.

BRIEF DESCRIPTION OF THE DRAWING

The FIGURE is a three-dimensional comparison of mean crystallite length parallel to the direction of the 12-ring channels, mesopore volume and conversion obtained with several samples.

DETAILED DESCRIPTION OF THE INVENTION

The UZM-14 of the present invention is a novel aluminosilicate zeolite with unique adsorption properties and catalytic activity, having a MOR framework type as described in *Atlas of Zeolite Framework Types, 6th Revised Edition*, C. H. Baerlocher, L. B. McCusker, and D. H. Olson, editors, Elsevier (2007), pp. 218-219. The MOR structure comprises four- and five-membered rings of the $SiO_4$ and $AlO_4$ tetrahedra so arranged that the crystal lattice comprises 12-ring channels running parallel along the crystal axis to give a tubular configuration. The zeolite usually is characterized by a silica-alumina mole ratio of from about 8 to about 50, and preferably is no more than about 30. The invention is based on the discovery that specific crystal characteristics allow increased accessibility to the internal micropore volume for improved activity and selectivity in transalkylating aromatics.

The UZM-14 aggregate material of the invention features one or more of the following distinctive characteristics:

(1) globular aggregates have a mesopore volume of at least about 0.10 cc/gram, preferably at least about 0.13 cc/gram, and especially at least about 0.2 cc/gram;

(2) the UZM-14 crystallites have at least about $1 \times 10^{19}$ 12-ring-channel openings/gram of UZM-14 material;

(3) the mean crystallite length parallel to the direction of 12-ring channels is about 60 nm or less and preferably about 50 nm or less;

(4) The $Si/Al_2$ ratio of the UZM-14 aggregate material generally is between about 8 and about 50, and preferably is no more than about 30.

The UZM-14 of the invention has an empirical composition in the as-synthesized form on an anhydrous basis expressed by the empirical formula:

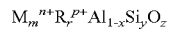

where M is at least one exchangeable cation and is selected from the group consisting of alkali and alkaline earth metals including but not limited to lithium, sodium, potassium, rubidium, cesium, calcium, strontium, barium and mixtures thereof. R is at least one organic cation selected from the group consisting of protonated amines, protonated diamines, quaternary ammonium ions, diquaternary ammonium ions, protonated alkanolamines, and quaternized alkanolammonium ions. Relating the components, "m" is the mole ratio of M to Al and varies from about 0.05 to about 0.95 "r" is the mole ratio of R to Al and has a value of about 0.05 to about 0.95, "n" is the weighted average valence of M and has a value of about 1 to about 2, "p" is the weighted average valence of R and has a value of about 1 to about 2, "y" is the mole ratio of Si to Al and varies from about 3 to about 50 and "z" is the mole ratio of O to Al and has a value determined by the equation:

$$z=(m \cdot n+r \cdot p+3+4 \cdot y)/2$$

The UZM-14 aggregate material of the invention is prepared by a hydrothermal crystallization of a reaction mixture prepared by combining reactive sources of M, R, aluminum and silicon. The sources of aluminum include but are not limited to aluminum alkoxides, precipitated aluminas, aluminum metal, aluminum salts and alumina sols. Specific examples of aluminum alkoxides include, but are not limited to aluminum ortho sec-butoxide and aluminum ortho isopropoxide. Sources of silica include but are not limited to tetraethylorthosilicate, colloidal silica, precipitated silica, alkali silicates, HiSil and Ultrasil. Sources of the M metals include the halide salts, nitrate salts, acetate salts, and hydroxides of the respective alkali or alkaline earth metals. When R is a quaternary ammonium cation or a quaternized alkanolammonium cation, the sources include the hydroxide, chloride, bromide, iodide and fluoride compounds. Specific examples include without limitation tetraethylammonium hydroxide, tetraethylammonium bromide, diethyldimethylammonium hydroxide and the like. R may also be introduced as an amine, diamine, or alkanolamine such as N,N,N',N'-tetramethyl-1,6-hexanediamine, triethylamine, and triethanolamine.

The reaction mixture containing reactive sources of the desired components, optionally comprising UZM-14 seed, is reacted at a temperature of about 85° C. to about 225° C. and preferably from about 110° C. to about 170° C. for a period of about 1 day to about 2 weeks and preferably for a time of about 2 days to about 6 days in a sealed reaction vessel under autogenous pressure. Effective mixing at between about 100 and about 1000, and preferably about 200 to about 500, revolutions per minute is important for realization of the invention. After crystallization is complete, the solid product is isolated from the heterogeneous mixture by means such as filtration or centrifugation, and then washed with deionized water and dried in air at ambient temperature up to about 100° C.

As synthesized, the UZM-14 will contain some of the exchangeable or charge balancing cations in its channels. These exchangeable cations can be exchanged for other cations, or in the case of organic cations, they can be removed by heating under controlled conditions. Because UZM-14 is a large-pore zeolite, it is also possible to remove some organic cations directly by ion exchange, for example by aqueous ammoniacal treatment at a pH of from about 10 to about 12.

The catalyst of the invention generally comprises a refractory inorganic-oxide binder and a metal component. The catalyst also preferably has been subjected to a presulfiding step to incorporate from about 0.05 to about 2 wt.-% sulfur on an elemental basis.

The inorganic-oxide binder component of the invention comprises such materials as alumina, silica, zirconia, titania, thoria, boria, magnesia, chromia, stannic oxide, and the like as well as combinations and composites thereof, for example alumina-silica, alumina-zirconia, alumina-titania, aluminum phosphate, and the like. The binder preferably comprises one or more of alumina, silica and silica-alumina. Alumina is an especially preferred refractory inorganic oxide for use herein, particularly with respect to the manufacture of a catalytic composite for use in the transalkylation of alkylaromatic hydrocarbons. The alumina may be any of the various hydrous aluminum oxides or alumina gels such as alpha-alumina monohydrate of the boehmite structure, alpha-alumina trihydrate of the gibbsite structure, beta-alumina trihydrate of the bayerite structure, and the like, the first mentioned alpha-alumina monohydrate being preferred.

The binder and zeolite may be combined in any conventional or otherwise convenient manner to form spheres, pills, pellets, granules, extrudates, or other suitable particle shape. For example, finely divided zeolite and metal salt particles can be dispersed in an alumina sol, and the mixture in turn dispersed as droplets in a hot oil bath whereby gelation occurs with the formation of spheroidal gel particles. The method is described in greater detail in U.S. Pat. No. 2,620,314. A preferred method comprises commingling a finely divided form of the selected zeolite, refractory inorganic oxide and a metal salt with a binder and/or lubricant and compressing the mixture into pills or pellets of uniform size and shape. Alternatively, and still more preferably, the zeolite, refractory inorganic oxide and metal salt are combined and admixed with a peptizing agent in a mix-muller, a dilute nitric acid being one example of the suitable peptizing agent. The resulting dough can be pressured through a die or orifice of predetermined size to form extrudate particles which can be dried and calcined and utilized as such. A multitude of different extrudate shapes are possible, including, but not limited to, cylinders, cloverleaf, dumbbell and symmetrical and asymmetrical polylobates, with a trilobe form being favored. The extrudates also may be formed into spheres by means of a spinning disc or drum and then dried and calcined.

The catalyst of the invention optionally may comprise an additional zeolitic component, The additional zeolite component preferably is selected from one or more of MFI, MEL, EUO, FER, MFS, MOR, MTT, MTW, MWW, MAZ, TON and FAU (IUPAC Commission on Zeolite Nomenclature) and UZM-8 (see WO 2005/113439, incorporated herein by reference thereto). More preferably, particularly when the catalyst is used in a transalkylation process, the additional zeolitic component consists essentially of MFI. Suitable total zeolite amounts in the catalyst range from about 1 to about 100 wt-%, preferably from about 10 to about 95 wt-%, and more preferably between about 60 and about 90 wt-%.

The catalyst preferably comprises a metal component comprising one or more elements selected from groups VIB(6), VIIB(7), VIII(8-10), IB(11), IIB(12), IIIA(13) and IVA(14) of the Periodic Table. Preferably the metal component is selected from one or more of rhenium, nickel, cobalt, molybdenum and tungsten when the catalyst is used in a transalkylation process. Especially preferred metal components comprise one or both of nickel and molybdenum. Suitable metal amounts in the transalkylation catalyst range from about 0.01 to about 15 wt-% on an elemental basis, with the range from about 0.1 to about 12 wt-% being preferred, and the range from about 0.1 to about 10 wt-% being highly preferred. The catalyst also may comprise a phosphorus component, and an optional binder comprises aluminum phosphate as described in U.S. Pat. No. 6,008,423 which is incorporated herein by reference thereto. The catalyst also preferably has been subjected to a presulfiding step to incorporate from about 0.05 to about 2 wt.-% sulfur on an elemental basis. This presulfiding step may take place either during the manufacture of the catalyst or after the catalyst has been loaded into a process unit.

The finished composite is preferably calcined in an air atmosphere at a temperature of from about 425° to about 750°

C., preferably at a temperature of from about 475° to about 550° C., over a period of from about 0.5 to about 10 hours.

The UZM-14 aggregate material of the invention can be used in catalysts to effect a variety of reactions known in the art. These include without limitation cracking, hydrocracking, alkylation of both aromatics and isoparaffins, isomerization, polymerization, reforming, dewaxing, hydrogenation, dehydrogenation, transalkylation, dealkylation, hydration, dehydration, hydrotreating, hydrodenitrogenation, hydrodesulfurization, methanation and syngas shift process. Preferred hydrocarbon conversion processes include alkylation of aromatics and isoparaffins and isomerization of aromatics and, especially, transalkylation of aromatics.

Hydrocracking conditions typically include a temperature in the range of 200° to 650° C., preferably between 310° and 510° C. Reaction pressures are in the range of atmospheric to about 25 MPa, and preferably between 1.4 and 20 MPa gauge. Contact times usually correspond to liquid hourly space velocities (LHSV) in the range of about 0.1 to 15 $hr^{-1}$, preferably between about 0.2 and 3 $hr^{-1}$. Hydrogen circulation rates are in the range of 180 to 9000 std. $m^3/m^3$, preferably between 350 and 5000 std. $m^3/m^3$. Suitable hydrotreating conditions are generally within the broad ranges of hydrocracking conditions set out above.

Catalytic cracking processes preferably convert feedstocks such as gas oils, heavy naphthas, and deasphalted residual oils to gasoline as the principal desired product. Temperature conditions of 450° to 600° C., LHSV of 0.5 to $hr^{-1}$ and pressure of from about atmospheric to 350 kPa are suitable.

Alkylation of isoparaffins with olefins to produce alkylates suitable as motor fuel components is carried out at temperatures of −30° to 40° C., pressures from about atmospheric to about 7 MPa and a weight hourly space velocity (WHSV) of 0.1 to about 120 $hr^{-1}$. Details on paraffin alkylation may be found in U.S. Pat. Nos. 5,157,196 and 5,157,197, which are incorporated by reference.

Other reactions may be catalyzed by catalysts comprising UZM-14, including the reforming of naphtha to gasoline, dehydrogenation of ethylbenzene to styrene, hydrogenation of benzene to cyclohexane, base-catalyzed side chain alkylation of alkylaromatics, aldol-condensations, olefin double bond isomerization and isomerization of acetylenes, alcohol dehydrogenation, and olefin dimerization, oligomerization and conversion of alcohol to olefins. Suitably ion-exchanged forms of these materials can catalyze the reduction of $NO_x$ to $N_2$ in automotive and industrial exhaust streams. Some of the reaction conditions and types of feeds that can be used in these processes are set forth in U.S. Pat. No. 5,015,796 and in H. Pines, The Chemistry Of Catalytic Hydrocarbon Conversions, Academic Press (1981) pp. 123-154 and references contained therein, which are incorporated herein by reference.

The zeolite of this invention is capable of separating mixtures of molecular species based on the molecular size (kinetic diameter; separation is accomplished by the smaller molecular species entering the intracrystalline void space while excluding larger species). The kinetic diameters of various molecules such as oxygen, nitrogen, carbon dioxide, carbon monoxide and various hydrocarbons are provided in D. W. Breck, Zeolite Molecular Sieves, John Wiley and Sons (1974) p. 636. Hydrocarbons also may be separated based on molecular size.

The alkylation, preferably the monoalkylation, of aromatic compounds involves reacting an aromatic compound with an olefin using the above described zeolitic catalyst. The olefins which can be used in the instant process are any of those which contain from 2 up to about 20 carbon atoms. These olefins may be branched or linear olefins and either terminal or internal olefins. Preferred olefins are ethylene, propylene and those olefins known as detergent-range olefins containing from 6 up through about 20 carbon atoms which have either internal or terminal double bonds. The reaction is conducted under at least partial liquid phase conditions. Therefore, the reaction pressure is adjusted to maintain the olefin at least partially dissolved in the liquid phase. For higher olefins the reaction may be conducted at autogenous pressure. As a practical matter the pressure normally is in the range between about 1.4 and 7 MPa, but usually is in a range between about 2 and 4 MPa. The alkylation of the alkylatable aromatic compounds with the olefins in the $C_2$ to $C_{20}$ range can be carried out at a temperature of about 60° C. to about 400° C., and preferably from about 90° C. to about 250° C., with about 0.1 to about 3 $hr^{-1}$ weight hourly space velocity with respect to the olefin. The alkylation of benzene with ethylene can be carried out at temperatures of about 200° C. to about 250° C. and the alkylation of benzene by propylene at a temperature of about 90° C. to about 200° C. The ratio of alkylatable aromatic compound to olefin used in the process will depend upon the particular reaction. For alkylation of benzene with ethylene or propylene, benzene-to-olefin ratios may be between about 1 and about 10. For detergent range olefins, a benzene-to-olefin ratio of between about 5:1 and about 30:1 is generally sufficient to ensure the desired monoalkylation selectivity.

Isomerization of alkylaromatics, and particularly of a $C_8$-aromatic mixture containing ethylbenzene and xylenes, is a preferred application of UZM-14-containing catalysts. The alkylaromatic feed mixture, preferably a non-equilibrium mixture of $C_8$ aromatics, is contacted with the isomerization catalyst at suitable alkylaromatic-isomerization conditions. Such conditions comprising a temperature ranging from about 0° to 600° C. or more, and preferably is in the range of from about 100° to 500° C. The pressure generally is from about atmospheric to 10 KPa absolute, preferably less than about 5 KPa. Sufficient catalyst is contained in the isomerization zone to provide a liquid hourly space velocity with respect to the hydrocarbon feed mixture of from about 0.1 to about 30 $hr^{-1}$, and preferably about 0.5 to 10 $hr^{-1}$. The hydrocarbon feed mixture optimally is reacted in admixture with hydrogen at a hydrogen/hydrocarbon mole ratio of about 0.5:1 to about 25:1 or more. Further details of the process may be found in U.S. Pat. No. 7,091,390, incorporated herein by reference thereto.

A catalyst comprising UZM-14 is particularly effective for the transalkylation and disproportionation of alkylaromatic hydrocarbons. Thus, an alkylaromatic hydrocarbon having from about 6 to about 15 carbon atoms per molecule is treated at transalkylation reaction conditions in contact with a catalyst comprising the UZM-14 of the invention to form products of higher and lower number of carbon atoms than said alkylaromatic hydrocarbon. The catalytic composite is particularly effective in the transalkylation of toluene and benzene with heavy aromatics to form high yields of xylenes.

The aromatics-rich feed stream to a transalkylation or disproportionation process may be derived from a variety of sources, including without limitation catalytic reforming, pyrolysis of naphtha, distillates or other hydrocarbons to yield light olefins and heavier aromatics-rich byproducts, and catalytic or thermal cracking of heavy oils to yield products in the gasoline range. Products from pyrolysis or other cracking operations generally will be hydrotreated according to processes well known in the industry before being charged to the complex in order to remove sulfur, olefins and other compounds which would affect product quality. Light cycle oil also may be beneficially hydrocracked to yield lighter components which can be reformed catalytically to yield the aromatics-rich feed stream. If the feed stream is catalytic reformate, the reformer preferably is operated at high severity for high aromatics yield with a low concentration of nonaromatics in the product. The reformate also advantageously is subjected to olefin saturation to remove potential product contaminants and materials that could polymerize to heavy nonconvertibles in a transalkylation process. Such processing steps are described in U.S. Pat. No. 6,740,788 B1, incorporated herein by reference thereto.

The transalkylation or disproportionation reaction can be effected in contact with the catalytic composite of this invention in any conventional or otherwise convenient manner and may comprise a batch or continuous type of operation, with a continuous operation being preferred. The catalyst usefully is disposed as a fixed bed in a reaction zone of a vertical tubular reactor with the alkylaromatic feed stock charged through the bed in an upflow or downflow manner. Conditions employed in the transalkylation zone normally include a temperature of from about 200° to about 540° C., preferably between about 200° to about 480° C. The transalkylation zone is operated at moderately elevated pressures broadly ranging from about 100 kPa to about 6 Mpa absolute. The transalkylation reaction can be effected over a wide range of space velocities, i.e., volume of charge per volume of catalyst per hour, liquid hourly space velocity generally is in the range of from about 0.1 to about 20 hr$^{-1}$. The feedstock is preferably transalkylated in the vapor phase and in the presence of hydrogen; if transalkylated in the liquid phase, then the presence of hydrogen is optional. If present, free hydrogen is associated with the feedstock and recycled hydrocarbons in an amount of about 0.1 moles per mole of alkylaromatics up to about 10 moles per mole of alkylaromatic. This ratio of hydrogen to alkylaromatic is also referred to as hydrogen to hydrocarbon ratio. The catalyst is particularly noteworthy for its relatively high stability at a high activity level.

The access of reactants to the 12-ring channels of the UZM-14 has been found to be the most important parameter affecting the activity and stability of the catalyst for transalkylation of aromatic hydrocarbons. This access has been found to relate to crystallite length, to mesopore volume and to 12-ring channel openings per unit of zeolite. The most important parameter apparently is crystallite length parallel to the direction of the 12-ring channels, which should be about 60 nm or less and preferably about 50 nm or less.

EXAMPLES

The following examples are based on test results and characteristics measured on ammonium-exchanged and calcined UZM-14. The appended claims embrace UZM-14 in any stage of manufacture or formulation including as-synthesized or before or after ion exchange and/or before or after calcination. The examples are presented as illustration of the invention and should not be construed as a limitation on the generally broad scope of the invention as set out in the appended claims.

Two samples of UZM-14 were prepared and designated as UZM-14A and UZM-14B in Example 1 for formulation of catalysts and detailed testing. The samples were prepared from NaOH, sodium aluminate, SiO$_2$ (Ultrasil) and tetraethylammonium bromide (TEABr) along with sufficient deionized water, and the crystallization was effected at the indicated temperature with agitation as indicated in revolutions per minute (RPM) over the indicated period of time. The resulting globular aggregates of crystallites were washed three times with deionized water and dried at a temperature of 100° C.

Example 1

|  | UZM-14-A | UZM-14-B |
|---|---|---|
| NaOH (g) | 625 | 625 |
| Na Aluminate (g) | 450 | 451 |
| SiO$_2$ (Ultrasil) (g) | 3212 | 3241 |
| TEABr (g) | 506 | 506 |
| H$_2$O (g) | 16,850 | 16,975 |
| Temperature (° C.) | 150 | 150 |
| Mixing (RPM) | 200 | 300 |
| Time (hr) | 66 | 76 |

Samples of known state-of-the-art mordenites were acquired from Zeolyst International and Tosoh Corporation for comparison with the UZM-14 samples. Characteristics of the two UZM-14 samples and the Zeolyst and Tosoh samples are compared in Example 2.

The mean crystallite length parallel to the direction of the 12-ring channels was measured by applying the Scherrer equation to x-ray diffraction data. Prior to analysis, each of the UZM-14 and the commercial mordenites were converted to the hydrogen form by heating the NH4-exchanged form to 540° C. for 2 hours in nitrogen and then for 5 hours in air. Specifically, the full width at half maximum (FWHM) was measured for the (002) diffraction peak of the MOR component at about 23.8° 2θ for CuKα radiation and then the mean crystallite length, L$_{002}$, parallel to the direction of the 12-ring channels was calculated from the Scherrer equation, $$L_{002}=0.9*\lambda/(\beta*\cos(\theta))$$

where λ is the wavelength for CuKα radiation, θ is one-half the diffraction angle, and β is the FWHM for the peak corrected for instrumental broadening, using the equation $$\beta^{1/2}=B^{1/2}-b^{1/2}$$

where B is the measured FWHM for the peak and b is the measured FWHM for an instrumental standard showing only instrumental broadening. It is assumed that the peaks are partially Gaussian and partially Cauchy in shape.

The number of 12-ring channel-openings per gram of MOR framework type zeolite, N$_p$, is inversely proportional to the mean crystallite length parallel to the direction of the 12-ring channels and was estimated from the equation $$N_p=(4*N^0*c)/(L_{002}*MW)$$

where N$^0$ is Avagadros number (6.023*10$^{23}$), c is the c-axis unit cell length, L$_{002}$, is the mean crystallite length parallel to the direction of the 12-ring channels, and MW is the molecular weight of the unit cell contents. For the present samples, this equation reduces to (with L$_{002}$ measured in nm)

$$N_p=6.2\times10^{20}/L_{002}$$

Particle sizes were estimated from high resolution SEM images. SEM particle sizes for the UZM-14 samples and for the commercial mordenites are in general larger than crystallite sizes since the particles can comprise multiple crystallites.

The mesopore volumes for each of these materials were determined from nitrogen sorption isotherms as follows. Prior to analysis, each of the UZM-14 and the commercial mordenites were converted to the hydrogen form by heating the NH4-exchanged form to 540° C. for 2 hours in nitrogen and then for 5 hours in air. The sorption isotherms were then measured and the total pore volume was determined from the nitrogen uptake at the highest value of $P/P_0$ (~0.98). The micropore volume was estimated using the t-plot. The mesopore volume was obtained by subtracting the micropore volume from the total pore volume.

For further testing, each of the UZM-14 powders and the commercial mordenite powders described above were formed into catalysts which contained 0.15% Re, 25% $Al_2O_3$ binder and 75% of the UZM-14 or commercial mordenite material. In a typical catalyst preparation, about 100 grams of ammonium exchanged zeolite was extruded with peptized Catapal B alumina to make a 75% zeolite/25% alumina formulation. The extrudates were calcined at 550° C. for 3 hours in air, then rotary impregnated with an aqueous HReO4 solution to target 0.15% Re on the catalyst. The Re containing extrudates were then calcined at 540° C. for 2 hours in air.

An activity test was carried out for each of these catalyst samples in an aromatics transalkylation test. The overall conversion, a weighed average of the transalkylation, dealkylation and disproportionation reactions, was measured at 350° C. at a reactor pressure=250 psig, a weight hourly space velocity=4 and a H2:HC ratio=6. The catalysts were sulfided in the test unit by doping the feed with excess dimethyl disulfide (250 ppm S) for the first hour of the test. The S/Re molar ratio on the spent catalysts is typically in the 0.5-0.8 range. The feed had nominally the following composition in weight percent:

|  |  |
|---|---|
| Toluene | 75 |
| Propylbenzene | 2 |
| Methylethylbenzene | 10 |
| Trimethylbenzene | 9.7 |
| Indane | 0.8 |
| Methylpropylbenzene | 1.0 |
| Diethylbenzene | 0.4 |
| Dimethylethylbenzene | 1.0 |
| $C_{11}$+ aromatics | 0.1 |

Comparative conversion results for the transalkylation of the aforementioned feed for each of these catalysts as well as characteristics of the Zeolyst and Tosoh samples are shown in Example 2.

Example 2

|  | UZM-14-A | UZM-14-B | Zeolyst CBV 21A | Tosoh HSZ-643NHA |
|---|---|---|---|---|
| $L_{002}$ (nm) | 47 | 50 | 68 | 78 |
| Number of 12-ring channel-openings per gram of zeolite | $1.4 \times 10^{19}$ | $1.3 \times 10^{19}$ | $0.91 \times 10^{19}$ | $0.79 \times 10^{19}$ |
| Mean particle size, nm | 106 | 81 | 167 | 170 |
| Maximum particle size, nm | 207 | 186 | 617 | 430 |
| 90% < (nm) | 175 | 143 | 273 | 299 |
| 80% < (nm) | 144 | 110 | 233 | 244 |
| 70% < (nm) | 129 | 99 | 209 | 198 |
| Mesopore Volume (cc/g) | 0.13 | 0.22 | 0.08 | 0.06 |
| Activity Test, % Conversion at 350° C. | 32.8 | 36.8 | 26.5 | 25.7 |

Example 3

Additional UZM-14 samples were prepared in similar manner of UZM-14A and UZM-14B with slight variations to the parameters discussed in Example 1, and the crystallite length parallel to the direction of the 12-ring channels, the mesopore volume, and the conversion were determined for each of the samples:

| Material | $L_{002}$ (nm) | Mesopore Volume (cc/g) | % Conversion at 350° C. |
|---|---|---|---|
| UZM-14-A | 46.6 | 0.13 | 32.8 |
| UZM14-B | 50.4 | 0.22 | 36.8 |
| UZM-14-C | 43.9 | 0.14 | 33.8 |
| UZM-14-D | 45.0 | 0.32 | 39.5 |
| UZM-14-E | 44.2 | 0.35 | 38.8 |
| UZM-14-F | 40.8 | 0.15 | 35.9 |
| UZM-14-G | 42.0 | 0.38 | 43.6 |
| UZM-14-H | 41.3 | 0.27 | 41.8 |
| UZM-14-I | 43.9 | 0.14 | 34.4 |
| UZM-14-J | 42.2 | 0.29 | 40.0 |
| UZM-14-K | 40.6 | 0.32 | 40.3 |
| UZM-14-L | 43.4 | 0.20 | 38.7 |
| Zeolyst | 68.2 | 0.08 | 26.5 |
| Tosoh | 77.9 | 0.06 | 25.7 |

The above results are shown in the attached three-dimensional FIGURE, with the vertical line below each point representing % conversion above the base of 25%. The above results clearly show the advantage of lower crystallite length parallel to the direction of the 12-ring channels and also of increased mesopore volume.

Example 4

The UZM-14-A and UZM-14-B materials described above were formed into catalysts by blending a mixture of 50% UZM-14, 25% MFI zeolite and 25% peptized Catapal B with a solution of nickel nitrate, ammonium heptamolybdate and phosphoric acid, to obtain catalysts with 0.45% Ni, 2% Mo and 0.3% P. After extrusion, the catalysts were calcined at 500° C. for 2 hours in air.

These catalysts were then tested for activity under identical conditions as used in Example 9, with the exception that the sulfiding phase was extended to 20 hours to allow enough time for complete sulfiding of the larger amount of metals. The resulting conversions at 350° C. were as follows:

| | |
|---|---|
| UZM-14-A | 39.7%. |
| UZM-14-B | 44.5%. |

Example 5

The as-synthesized UZM-14-B material was calcined for 12 hours in air at 550° C., ion-exchanged, and then calcined for an additional 12 hours at 550° C. Following this treatment, the total acidity of the material was 0.500 m-moles/g as determined by $NH_3$-TPD and 26% of the Al was non-framework as determined by Al-NMR. This demonstrates that the acidity of the UZM-14 material is thermally stable.

The invention claimed is:

1. A UZM-14 aggregate material comprising globular aggregates of crystallites having a MOR framework type comprising 12-ring channels, a silica-alumina mole ratio of from about 8 to no more than about 30, a mesopore volume of at least about 0.10 cc/gram, and a mean crystallite length parallel to the direction of the 12-ring channels of about 60 nm or less.

2. The UZM-14 aggregate material of claim 1 wherein the mean crystallite length parallel to the direction of the 12-ring channels is about 50 nm or less.

3. The UZM-14 aggregate material of claim 1 wherein the mesopore volume is at least about 0.13 cc/gram.

4. The UZM aggregate material of claim 1 wherein the UZM-14 crystallites have at least about $1\times10^{19}$ 12-ring-channel openings/gram of aggregate material.

5. A catalyst suitable for the conversion of aromatic hydrocarbons which comprises:
   (a) a UZM-14 aggregate material comprising globular aggregates of crystallites having a MOR framework type comprising 12-ring channels, a silica-alumina mole ratio of from about 8 to no more than about 30, a mesopore volume of at least about 0.10 cc/gram, mean crystallite length parallel to the direction of the 12-ring channels of about 60 nm or less and a binder selected from one or more of alumina, silica and silica-alumina; and,
   (b) a metal component comprising one or more elements selected from groups VIB(6), VIIB(7), VIII(8-10) and IVA(14) of the Periodic Table.

6. The catalyst of claim 5 wherein the mean crystallite length parallel to the direction of the 12-ring channels is about 50 nm or less.

7. The catalyst of claim 5 wherein the UZM-14 crystallites have at least about $1\times10^{19}$ 12-ring-channel openings/gram of aggregate material.

8. The catalyst of claim 5 wherein the mesopore volume of the UZM-14 aggregate material is at least about 0.13 cc/gram.

9. The catalyst of claim 5 further comprising a phosphorus component.

10. The catalyst of claim 5 wherein the binder comprises alumina.

11. The catalyst of claim 9 wherein the binder comprises aluminum phosphate.

12. The catalyst of claim 5 further comprising an oil-dropped spherical form.

13. The catalyst of claim 5 wherein the metal component is selected from one or more of rhenium, nickel, cobalt, molybdenum and tungsten.

14. The catalyst of claim 13 wherein the metal component consists essentially of at least one of rhenium, nickel and molybdenum.

15. The catalyst of claim 5 further having been subjected to a presulfiding step.

16. The catalyst of claim 5 further comprising an additional zeolitic component selected from one or more of MFI, MEL, EUO, FER, MFS, MTT, MTW, TON, MOR and FAU.

17. A catalyst suitable for the conversion of aromatic hydrocarbons which comprises:
   (a) a UZM-14 aggregate material comprising globular aggregates of crystallites having a MOR framework type comprising 12-ring channels, a silica-alumina mole ratio of from about 8 to no more than about 30, a mesopore volume of at least about 0.10 cc/gram, and a mean crystallite length parallel to the direction of the 12-ring channels of about 60 nm or less,
   (b) an additional zeolitic component selected from one or more of MFI, MEL, EUO, FER, MFS, MTT, MTW, TON, MOR and FAU;
   (c) a binder selected from one or more of alumina, silica and silica-alumina; and,
   (d) a metal component comprising one or more elements selected from groups VIB(6), VIIB(7), VIII(8-10), 1B(11) and IVA(14) of the Periodic Table.

18. The catalyst of claim 17 wherein the additional zeolitic component is selected from one or both of MFI and MOR.

* * * * *